United States Patent
Sun et al.

(10) Patent No.: US 11,684,692 B2
(45) Date of Patent: *Jun. 27, 2023

(54) ABSORBABLE IRON-BASED INSTRUMENT

(71) Applicant: Biotyx Medical (Shenzhen) Co., Ltd., Shenzhen (CN)

(72) Inventors: Hongtao Sun, Shenzhen (CN); Deyuan Zhang, Shenzhen (CN); Jun Hu, Shenzhen (CN); Liping Chen, Shenzhen (CN)

(73) Assignee: Lifetech Scientific (Shenzhen) Co. Ltd., Shenzhen (CN)

( * ) Notice: Subject to any disclaimer, the term of this patent is extended or adjusted under 35 U.S.C. 154(b) by 561 days.

This patent is subject to a terminal disclaimer.

(21) Appl. No.: 16/473,896

(22) PCT Filed: Dec. 19, 2017

(86) PCT No.: PCT/CN2017/117214
§ 371 (c)(1),
(2) Date: Jun. 26, 2019

(87) PCT Pub. No.: WO2018/121350
PCT Pub. Date: Jul. 5, 2018

(65) Prior Publication Data
US 2020/0384149 A1    Dec. 10, 2020

(30) Foreign Application Priority Data
Dec. 30, 2016   (CN) .................. 201611262095.X (51) Int. Cl.
*A61L 27/04*    (2006.01)
*A61L 27/34*    (2006.01)
*A61L 27/54*    (2006.01)
*A61L 27/58*    (2006.01)
*A61L 17/10*    (2006.01)
*A61L 17/00*    (2006.01)
*A61L 31/02*    (2006.01)
*A61L 31/06*    (2006.01)
*A61L 31/14*    (2006.01)
*A61L 31/16*    (2006.01)
*C08L 67/04*    (2006.01)
*A61K 45/06*    (2006.01)

(52) U.S. Cl.
CPC ............ *A61L 27/04* (2013.01); *A61L 17/005* (2013.01); *A61L 17/105* (2013.01); *A61L 27/34* (2013.01); *A61L 27/54* (2013.01); *A61L 27/58* (2013.01); *A61L 31/022* (2013.01); *A61L 31/06* (2013.01); *A61L 31/148* (2013.01); *A61L 31/16* (2013.01); *C08L 67/04* (2013.01); *A61K 45/06* (2013.01); *A61L 2300/41* (2013.01); *A61L 2300/416* (2013.01); *A61L 2300/42* (2013.01)

(58) Field of Classification Search
CPC ...... C08L 67/04; A61L 2300/42; A61L 27/04; A61L 27/042; A61L 27/306; A61L 27/54; A61L 27/58; A61L 31/022; A61L 31/148; A61L 17/105; A61L 2300/41; A61L 2300/416
See application file for complete search history.

(56) References Cited

U.S. PATENT DOCUMENTS

| | | | |
|---|---|---|---|
| 7,214,759 B2 * | 5/2007 | Pacetti ................. | C08G 63/181 528/480 |
| 9,394,612 B2 | 7/2016 | Bayer et al. | |
| 10,058,639 B2 | 8/2018 | Zhang et al. | |
| 11,020,514 B2 | 6/2021 | Qi et al. | |
| 2005/0209680 A1 | 9/2005 | Gale | |
| 2006/0198868 A1 * | 9/2006 | DeWitt ................... | A61L 31/10 424/426 |
| 2006/0229711 A1 * | 10/2006 | Yan .......................... | A61F 2/02 623/1.38 |
| 2010/0324654 A1 | 12/2010 | Bayer et al. | |
| 2018/0326128 A1 | 11/2018 | Qi et al. | |
| 2019/0022284 A1 | 1/2019 | Qi et al. | |
| 2020/0230296 A1 | 7/2020 | Sun et al. | |

FOREIGN PATENT DOCUMENTS

| | | |
|---|---|---|
| CN | 10222872 A | 11/2011 |
| CN | 102228721 A | 11/2011 |
| CN | 102228721 A | 11/2011 |
| CN | 104587534 A | 5/2015 |

(Continued)

OTHER PUBLICATIONS

International Search Report dated Mar. 27, 2018 for corresponding PCT Application No. PCT/CN2017/117214.
Office Action dated Jun. 1, 2020 for corresponding China Application No. 201611262095.X.
Search Report dated Jul. 23, 2020 for corresponding European Application No. EP 17887162.
Office Action dated Dec. 23, 2020 for corresponding India Application No. 201917027904.
Response dated Jun. 22, 2021 for corresponding India Application No. 201917027904.

(Continued)

*Primary Examiner* — Anna R Falkowitz
(74) *Attorney, Agent, or Firm* — Raymond Sun (57) ABSTRACT

An absorbable iron-based instrument is provided having an iron-based substrate, a zinc-containing protector in contact with the iron-based substrate, and a degradable polyester in contact with the iron-based substrate and/or the zinc-containing protector. The range of the ratio of the mass of the zinc-containing protector to the mass of the iron-based substrate is 1:200 to 1:2. In the degradable polyester, the mass fraction of a low-molecular-weight part with a molecular weight of less than 10,000 is less than or equal to 5%; alternatively, in the degradable polyester, the mass fraction of a residual monomer is less than or equal to 2%.

10 Claims, 3 Drawing Sheets

(56) References Cited

FOREIGN PATENT DOCUMENTS

| CN | 104587535 A | | 5/2015 | |
|----|-------------|---|--------|---|
| CN | 104587535 A | | 5/2015 | |
| CN | 105597163 A | | 5/2016 | |
| CN | 105839067 A | | 8/2016 | |
| CN | 105597163 A | | 5/2019 | |
| WO | WO2015/062546 | * | 5/2015 | ............... A61F 2/82 |

OTHER PUBLICATIONS

Notice of Allowance dated Oct. 26, 2021 for corresponding India Application No. 201917027904.
Grant Certificate for corresponding India Application No. 201917027904.

* cited by examiner

ABSORBABLE IRON-BASED INSTRUMENT

TECHNICAL FIELD

The present application belongs to the field of implantable medical devices, and more particularly relates to an absorbable iron-based device.

BACKGROUND ART

An absorbable implantable device supports or connects a lesion after being implanted into a human body, and is gradually corroded or degraded, and completely absorbed by organs until the lesion is cured or recovers its normal shape and functions. According to different application sites of the implantable device, the recovery period of the lesion is generally considered to be 1 to 6 months; that is, within this period of time after implantation, the device is required to maintain a structural integrality and have a sufficient mechanical property to support or connect the lesion. However, after the device is implanted for 1 to 6 months, when the lesion is cured, the device should be corroded or degraded as fast as possible within a relatively short time.

Absorbable implantable devices made of an iron-based material which have good biocompatibility are widely used in various clinical applications. However, due to the slow corrosion rate of the iron-based material, the iron-based device remains in the human body for a long time after the lesion is cured, thereby increasing the possibility of long-term adverse reactions.

In the prior art, the surface of the iron-based device is coated with a degradable polyester coating layer to accelerate the corrosion of the iron-based device. The degradation of the degradable polyester coating layer in the body forms a weak-acid environment near the implant site to accelerate the corrosion of the iron-based device, but the weak-acid environment would also accelerate the degradation of degradable polyester, and the fast degradation of the degradable polyester would result in extremely fast corrosion of the iron-based device during the early stages of implantation, thus affecting the structural integrality and the mechanical property of the iron-based device within the first 1 to 6 months after implantation. At the moment, it is necessary to slow the early corrosion of the iron-based device to guarantee the biological safety of the device.

SUMMARY OF THE INVENTION

In view of this, it is necessary to provide an absorbable iron-based device. A zinc-containing protector and degradable polyester are loaded on the device at the same time. The device may be allowed to maintain a structural integrality for 1 to 6 months under the protection of the zinc-containing protector by controlling the early degradation of the degradable polyester, so as to provide a supporting force or a connecting force for the lesion. In addition, the production of a large number of zinc ions caused by fast and concentrated corrosion of the zinc-containing protector is avoided to effectively avoid the influence on the biological safety of the device caused by the cytotoxicity of a large number of zinc ions. Furthermore, after being implanted for 1 to 6 months, the device may be quickly corroded, so as to reduce the possibility of adverse reactions caused by long-term retention of the iron-based device in a human body.

A degradation process of the degradable polyester is related to the content of a residual monomer and a molecular weight distribution in the degradable polyester. In the present application, the zinc-containing protector and the degradable polyester are loaded on an iron-based substrate at the same time, so the degradation process of the degradable polyester during the early stages of implantation is controlled by adjusting the content of the residual monomer in the degradable polyester or the content of a low molecular weight portion in the degradable polyester, and then the corroding processes of the zinc-containing protector and the iron-based substrate during the early stages of implantation can be controlled. Therefore, during the early stages of implantation of the device, the degradable polyester promotes the zinc-containing protector to be corroded at a proper rate, and the zinc-containing protector may protect the iron-based substrate to allow the iron-based substrate to be slowly corroded, and even not corroded, within 1 to 6 months after the implantation. Meanwhile, in the corroding process of the zinc-containing protector, release of a large number of zinc ions may be avoided, so as to avoid the cytotoxicity generated by the zinc ions. Furthermore, when the device has been implanted for 1 to 6 months, the mass retention rate of the degradable polyester is more than or equal to 30 percent, so as to ensure that there is still sufficient degradable polyester to accelerate the corrosion of the iron-based substrate after the device has been implanted for 1 to 6 months, and then to reduce the possibility of the adverse reactions caused by the long-term retention of the iron-based device in the human body.

The present application provides an absorbable iron-based device, including an iron-based substrate, a zinc-containing protector in contact with the iron-based substrate, and degradable polyester in contact with the iron-based substrate and/or the zinc-containing protector. The ratio of the mass of the zinc-containing protector to the mass of the iron-based substrate ranges between 1:200 and 1:2. In the degradable polyester, the mass fraction of the low molecular weight portion is less than or equal to 5 percent, and the molecular weight of the low molecular weight portion is less than 10,000. Alternatively, in the degradable polyester, the mass fraction of the residual monomer is less than or equal to 2 percent.

In one embodiment, the mass fraction of the residual monomer is less than or equal to 1 percent. Under the same unit mass, the molecular number of a monomer is much greater than that of a polymer and the monomer is easier to ionize than the polymer to produce acidic hydrogen ions, so that the mass fraction of the residual monomer in the degradable polyester has a relatively large impact on the early degradation process of the degradable polyester. When the mass fraction of the residual monomer of the degradable polyester is less than or equal to 1 percent, the acidity around the iron-based device in the early stages of implantation may be effectively lowered so as to allow the zinc-containing protector covering the surface of the iron-based substrate to be corroded at a proper rate, and allow the iron-based substrate located below the zinc-containing protector to be only slowly corroded and even barely corroded. In addition, the rapid corrosion of the zinc-containing protector can be avoided, thereby avoiding the release of a large amount of zinc ions, which causes cytotoxicity and affects the biosafety of the device.

In one embodiment, the mass fraction of the residual monomer is less than or equal to 0.1 percent.

In one embodiment, the mass fraction of the low molecular weight portion is less than or equal to 2 percent. The low molecular weight portion in the degradable polyester is more easily degraded into soluble oligomers during the early stages of degradation, so that reducing the mass fraction of the low molecular weight portion in the degradable polyester can effectively reduce the acidity around the iron-based device during the early stages of degradation, so as to allow the zinc-containing protector covering the surface of the iron-based substrate to be corroded during the early stages of implantation and allow the iron-based substrate located below the zinc-containing protector to be only slowly corroded, and even barely corroded. In addition, the relatively small mass fraction of the low molecular weight portion may ensure that there is still sufficient degradable polyester to accelerate the corrosion of the iron-based substrate after the device has been implanted for 1 to 6 months, and then avoid the long-term adverse reactions caused by the long-term retention of the device in the human body.

In one embodiment, the molecular weight of the low molecular weight portion is less than 100,000.

In one embodiment, the degradable polyester is obtained by separating and/or purifying raw materials of the degradable polyester by a precipitation method, gel permeation chromatography, an ultrafiltration film filtration method or an extraction method.

In one embodiment, the ratio of the mass of the degradable polyester to the mass of the iron-based substrate ranges between 1:1 and 1:200. Within this range of the ratio of the mass of the degradable polyester to the mass of the iron-based substrate, the corrosion period of the iron-based device may be shortened, and then the long-term adverse reactions caused by the long-term retention of the device in the human body is effectively avoided.

In one embodiment, the ratio of the mass of the degradable polyester to the mass of the iron-based substrate ranges between 1:6 and 1:100.

In one embodiment, the zinc-containing protector is a zinc elementary substance or a zinc alloy.

In one embodiment, the ratio of the mass of the zinc-containing protector to the mass of the iron-based substrate ranges between 1:100 and 1:10. For the absorbable iron-based device loading the zinc-containing protector and the degradable polyester at the same time, the ratio of the mass of the zinc-containing protector to the mass of the iron-based substrate should be matched with the ratio of the mass of the degradable polyester to the mass of the iron-based substrate, which helps to prevent the zinc-containing protector from failing to protect the iron-based device to maintain the structural integrity for 1 to 6 months after implantation, and also avoid the cytotoxicity generated by having a large number of zinc ions produced by the corrosion of the zinc-containing protector.

In one embodiment, the degradable polyester is selected from the group consisting of polylactic acid, polyglycolic acid, poly(butylene succinate), polyhydroxyalkanoate, polycaprolactone, polyethylene glycol adipate, a polylactic-glycolic acid copolymer or a polyhydroxybutyrate valerate copolymer, or is formed by copolymerizing at least two of monomers constituting the polylactic acid, the polyglycolic acid, the poly(butylene succinate), the polyhydroxyalkanoate, the polycaprolactone, the polyethylene glycol adipate, the polylactic-glycolic acid copolymer or the polyhydroxybutyrate valerate copolymer.

In one embodiment, the degradable polyester is formed by blending at least one of the polylactic acid, the polyglycolic acid, the poly(butylene succinate), the polyhydroxyalkanoate, the polycaprolactone, the polyethylene glycol adipate, the polylactic-glycolic acid copolymer or the polyhydroxybutyrate valerate copolymer with at least one of polyanhydride, poly(malate), starch, chitosan, cellulose, glycan or a glycan derivative, or is formed by copolymerizing at least one of monomers constituting the polylactic acid, the polyglycolic acid, the poly(butylene succinate), the polyhydroxyalkanoate, the polycaprolactone, the polyethylene glycol adipate, the polylactic-glycolic acid copolymer or the polyhydroxybutyrate valerate copolymer with at least one of monomers constituting the polyanhydride, the poly(malate), the starch, the chitosan, the cellulose, the glycan or the glycan derivative.

In one embodiment, the degradable polyester is formed by copolymerizing at least one of monomers constituting the polylactic acid, the polyglycolic acid, the poly(butylene succinate), the polyhydroxyalkanoate, the polycaprolactone, the polyethylene glycol adipate, the polylactic-glycolic acid copolymer or the polyhydroxybutyrate valerate copolymer with at least one of monomers constituting polyurethane, polycarbonate, polymethyl methacrylate, polystyrene, polybutylene or poly-n-butyl methacrylate.

In one embodiment, the zinc-containing protector is in contact with the iron-based substrate in at least one of the following manners: the zinc-containing protector at least partially covers the surface of the iron-based substrate, or the iron-based substrate is provided with gaps, grooves or holes, and the zinc-containing protector is arranged in the gaps, grooves or holes.

In one embodiment, the degradable polyester is in contact with the iron-based substrate in at least one of the following manners: the degradable polyester at least partially covers the surface of the iron-based substrate, or the iron-based substrate is provided with gaps, grooves or holes, and the degradable polyester is arranged in the gaps, grooves or holes, or the iron-based substrate has an inner cavity, and the inner cavity is filled with the degradable polyester.

Specifically, when the zinc-containing protector covers the entire surface of the iron-based substrate, the degradable polyester may cover the surface of the zinc-containing protector; that is, the degradable polymer is only in contact with the zinc-containing protector.

When the zinc-containing protector covers a portion of the surface of the iron-based substrate, the degradable polyester may only cover the surface of the zinc-containing protector; that is, the degradable polymer is only in contact with the zinc-containing protector.

When the zinc-containing protector covers a portion of the surface of the iron-based substrate, the degradable polyester may cover the surface of the zinc-containing protector and cover other portions of the surface of the iron-based substrate which are not covered by the zinc-containing protector; that is, the degradable polymer is in contact with the zinc-containing protector and the iron-based substrate.

When the zinc-containing protector covers part of the surface of the iron-based substrate, the degradable polyester may cover part of the surface of the iron-based substrate which is not covered by the zinc-containing protector; that is, the degradable polymer is only in contact with the iron-based substrate.

When the iron-based substrate is provided with the gaps, grooves or holes, in which the zinc-containing protector is arranged, the degradable polyester may only cover the surface of the zinc-containing protector; that is, the degradable polyester is only in contact with the zinc-containing protector.

When the iron-based substrate is provided with the gaps, grooves or holes, in part of which the zinc-containing protector is arranged, the degradable polyester may be arranged in other gaps, grooves or holes; that is, the degradable polyester is only in contact with the iron-based substrate.

When the iron-based substrate is provided with the gaps, grooves or holes, in which the zinc-containing protector is arranged, the degradable polyester may cover the entire surface of the iron-based substrate; that is, the degradable polyester is in contact with the zinc-containing protector and the iron-based substrate.

When the iron-based substrate is provided with a cavity filled with the degradable polyester, the zinc-containing protector may cover at least part of the outer surface of the iron-based substrate; that is, the degradable polyester is only in contact with the iron-based substrate.

In one embodiment, the iron-based substrate may be made of pure iron or an iron-based alloy, and the carbon content of the iron-based alloy is less than or equal to 2.11 percent.

In one embodiment, the absorbable iron-based device further includes an active drug. The active drug is mixed with the degradable polyester at a mass ratio of 1:(0.2-20).

In one embodiment, the active drug is selected from the group consisting of a drug for inhibiting vascular proliferation, an antiplatelet drug, an antithrombotic drug, an anti-inflammatory reaction drug or an antisensitization drug. The drug for inhibiting the vascular proliferation is selected from the group consisting of taxol, a taxol derivative, sirolimus or a sirolimus derivative. The antiplatelet drug is cilostazol. The antithrombotic drug is heparin. The anti-inflammatory reaction drug is dexamethasone. The antisensitization drug is selected from the group consisting of diphenhydramine, chlorpheniramine, promethazine, hydrocortisone, triamcinolone, methylprednisolone, clarityne, fexofenadine, levocetirizine, mizolastine or ebastine.

In one embodiment, the absorbable iron-based device includes a vascular stent, a non-endovascular stent, an occluder, an orthopaedic implant, a dental implant, a respiratory implant, a gynecological implant, an andrological implant, a suture or a bolt. The non-endovascular stent includes a tracheal stent, an esophageal stent, a urethral stent, an intestinal stent or a biliary stent. The orthopaedic implant includes a fixing screw, a fixing rivet or a bone plate.

According to the absorbable iron-based stent of the present application, the zinc-containing protector and the degradable polyester are loaded on the iron-based substrate, the degradation process of the degradable polyester during the early stages of implantation of the device is controlled by adjusting the content of the residual monomer in the degradable polyester or the content of the low molecular weight portion in the degradable polyester, and then the corroding processes of the zinc-containing protector and the iron-based substrate during the early stages of implantation are controlled. Compared with the prior art, the present application at least has the following beneficial effects:

(1) within 1 to 6 months after the absorbable iron-based device provided by the present application is implanted, the degradable polyester promotes the zinc-containing protector to be corroded at a proper rate to allow the zinc-containing protector to be completely corroded within 1 to 6 months after the implantation, and allow the iron-based substrate to be slowly corroded, and maybe even not corroded, under the protection of the zinc-containing protector, so as to meet the clinical requirement for the mechanical property of the implantable device in the early stage of implantation;

(2) the absorbable iron-based device provided by the present application does not produce a large number of zinc ions in the corroding process of the zinc-containing protector, so as to avoid the cytotoxicity generated by a large number of zinc ions and the influence on the biological safety of the device; and (3) when the absorbable iron-based device provided by the present application is implanted for 1 to 6 months, the mass retention rate of the degradable polyester is more than or equal to 30 percent, so as to ensure that there is still sufficient degradable polyester to accelerate the corrosion of the iron-based substrate after the device has been implanted for 1 to 6 months, and then to reduce the possibility of the adverse reactions caused by the long-term retention of the iron-based substrate in the human body.

DETAILED DESCRIPTION OF THE INVENTION

First, detection methods of a zinc-containing protector, degradable polyester and an absorbable iron-based device which are related to the present application are described below.

Detection Method of the Mass of the Degradable Polyester and the Mass of the Zinc-Containing Protector The mass of the degradable polyester is measured by the following weight loss method: the total mass $M_0$ of an absorbable iron-based device is measured; the degradable polyester is removed from the surface of the zinc-containing protector by using a good solvent (such as ethyl acetate or tetrahydrofuran) for the degradable polyester; the mass $M_{iron+zinc}$ of the residual absorbable iron-based device is weighted; and then the zinc-containing protection is removed from the surface of an iron-based substrate by using a sodium hydroxide solution at a concentration of 1 mol/L, and the mass $M_{iron}$ of the iron-based substrate is weighed. Therefore, the mass $M_{polyester}$ of the degradable polyester is $(M_0-M_{iron+zinc})$, and the mass $M_{zinc}$ of the zinc-containing protector is $(M_{iron+zinc}-M_{iron})$.

Detection Method of the Mass Fraction of a Residual Monomer in the Degradable Polyester First, the mass $M_{polyester}$ of the degradable polyester is measured by the above-mentioned weight loss method, which is $M_0-M_{iron+zinc}$, and the mass $M_{monomer}$ of the residual monomer in the degradable polyester is detected through gel permeation chromatography (GPC). Detection conditions are as follows:

an Agilent 7820A type gas chromatograph of Agilent Technologies is used, and a chromatographic column CD-ACID WAX (size: 30 m×0.32 mm, 0.50 micron) of Shanghai ANPEL is used. Column temperature and heating conditions are as follows: the column is heated from 50° C. to 180° C. at a heating rate of 20° C./min, and the temperature is maintained for 5 min; and then the column is heated from 180° C. to 200° C. at a heating rate of 10° C./min, and the temperature is maintained for 6.5 min. A sample injection chamber is at 200° C. A detector is at 250° C. The column flow velocity is 1.8 mL/min. The diversion ratio is 2:1. Make-up gas is 25 mL/min. The hydrogen flow is 30 mL/min. The air flow is 300 mL/min.

The mass fraction of the residual monomer in the degradable polyester=$M_{monomer}/(M_0-M_{iron+zinc})\times 100\%$ Detection Method of a Weight-Average Molecular Weight and a Molecular Weight Distribution of the Degradable Polyester The weight-average molecular weight and the molecular weight distribution of the degradable polyester are detected by use of a GPC-multiangle laser light scattering spectrometer combined molecular weight test system of Wyatt Company, USA. The test system includes a liquid phase pump and a sample injector of Agilent Company, USA, an Agilent PL MIXED-C type GPC column (size: 7.5×300 mm, 5 microns) of Agilent Company, and a multiangle laser light scattering spectrometer and a differential detector of Wyatt Company. Detection conditions are as follows: a flowing phase: tetrahydrofuran; a pump flow velocity: 1 mL/min; a sample injection volume: 100 uL; a laser wavelength: 663.9 nm; and test temperature: 35° C.

Mass Retention Rate of the Degradable Polyester

The mass retention rate of the degradable polyester refers to a ratio of the mass of the residual degradable polyester on the device after the absorbable iron-based device is corroded to the total mass of the degradable polyester before corrosion. The test of the mass retention rate specifically includes the following steps: before the absorbable implanted device is implanted, the mass $M_{polyester}$ of the degradable polyester is measured to be $(M_0-M_{iron+zinc})$ by the above-mentioned weight loss method; an absorbable iron-based device of the same specification is implanted into a blood vessel (such as a coronary artery, an abdominal aorta, an iliac artery or an inferior vena cava) of a small mammal (such as a rabbit, a dog or a pig); the residual device and a peripheral tissue thereof are removed at a predetermined observation time point, such as at the 6th month, the 9th month and the 12th month, to draw water from them until they are dried, and then are extracted with tetrahydrofuran, and the volume of an extract solution is fixed; the mass $m_{polyester}$ of the residual degradable polyester on the device by the above-mentioned GPC-multiangle laser light scattering spectrometer combined molecular weight test system of Wyatt Company; and the mass retention rate of the degradable polyester at this observation time point is m $m_{polyester}/(M_0-M_{iron+zinc})\times 100\%$.

Corrosion Condition of the Iron-Based Substrate

After the absorbable iron-based device is implanted into the body of an animal, the corrosion condition of the iron-based substrate is estimated according to a mass loss rate, specifically including the following steps: the absorbable iron-based device in which the mass of the iron-based substrate is $M_{iron}$ is implanted into the body of the animal; then the device and a peripheral tissue thereof are removed at a predetermined observation time point, such as at the 3rd month, the 6th month and the 12th month, and the tissue and the device are soaked in the sodium hydroxide solution at 1 mol/L to remove the residual zinc-containing protector and the degradable polyester and digest the tissue; the device is taken out from the sodium hydroxide solution and put into 3 percent tartaric acid solution for ultrasonic treatment to allow corrosion products attached to the device to completely fall off or be dissolved in a good solvent; the residual device is taken out, then dried and weighed to obtain the mass $m_{iron}$; and the mass loss rate of the iron-based substrate at this observation time point is $(M_{iron}-M_{iron})/M_{iron}\times 100\%$.

When the mass loss rate W of the iron-based substrate at a certain observation time point is less than 5 percent, it is considered that the iron-based substrate is not corroded within a time period from the implantation time point to this observation time point. When the mass loss rate W of the iron-based substrate at a certain observation time point is more than or equal to 90 percent, it is considered that the iron-based substrate is completely corroded, and a time period from the implantation time point to this observation time point is a corrosion period of the iron-based substrate.

Radial Supporting Force of the Absorbable Iron-Based Device

Clinically, the diastolic pressure (low pressure) and the systolic pressure (high pressure) of a coronary vessel of a normal person range between 60 to 120 mmHg, but the systolic pressure of a hypertension patient is up to 175 mmHg, namely 23.3 kPa. In case of coronary artery spasm, the systolic pressure of the blood vessel is 400 mmHg, namely 55 kPa. Thus, it is clinically considered that the effective support of the vascular stent to the coronary vessel refers to a stent that can at least bear the systolic pressure of 23.3 kPa in case of pulsation of the coronary vessel, and can at least bear the systolic pressure of 55 kPa in case of vasospasm.

An animal implantation test is used to investigate whether the radial supporting force of the absorbable iron-based device within 1 to 6 months of implantation into the body of the animal meets the clinical requirement for the mechanical property of the vascular stent or not, specifically including the following steps: the absorbable iron-based device is implanted into the blood vessel of a laboratory animal; then the absorbable iron-based device and a peripheral tissue thereof are removed at a predetermined observation time point, such as at the 1st month, the 3rd month and the 6th month; and after the water on the surface is drawn away completely, the radial supporting force test is directly carried out by using a radial supporting force tester from MSI Company.

Pathological analysis of the peripheral tissue of the absorbable iron-based device The peripheral tissue of the device is subjected to pathological analysis through H&E staining after the absorbable iron-based device has been implanted, specifically including the following steps: after the absorbable iron-based device has been implanted into the body of an animal, the absorbable iron-based device and a peripheral tissue thereof are removed at a predetermined observation time point, such as at the 1st month, the 3rd month and the 6th month, and are fixed with 10 percent formaldehyde solution at first, and then are embedded with resin; and multiple tissue sections are manufactured with a microtome and are subjected to H&E staining to observe the pathologic condition under a microscope.

In addition, it should be noted that the degradable polyester used in the technical solution of the present application may be a commercially available commodity capable of meeting the requirements for the mass fraction of the low molecular weight portion or the mass fraction of the residual monomer in the technical solution, and also may be a preparation sample obtained by those skilled in the art through conventional separation and/or purification for a commercially available degradable polyester raw material.

Separation and Purification Method of the Degradable Polyester

In the present application, the polyester raw material may be separated and/or purified through the following four methods, thereby obtaining the degradable polyester used in Embodiments 1 to 10. However, the separation and/or purification method of the degradable polyester is not limited to the following methods. The degradable polyester obtained by separating and/or purifying the degradable polyester raw material through any method may be applied to the absorbable iron-based device of the present application as long as the mass fraction of the low molecular weight portion or the residual monomer of the degradable polyester meets the requirements of the technical solution of the present application.

A precipitation method specifically includes the following steps: the degradable polyester raw material is dissolved into a good solvent (such as ethyl acetate, tetrahydrofuran, acetone, dichloromethane or chloroform) for the degradable polyester to obtain a degradable polyester solution; then a poor solvent (such as methanol, ethanol, isopropanol or water) for the degradable polyester, serving as a precipitant, is added into the degradable polyester solution and uniformly mixed with the degradable polyester solution, and at the moment, precipitates appear in the degradable polyester solution; liquid in the degradable polyester solution is poured out after the solution is placed for some time, and the precipitates are retained; and the precipitates are repeatedly precipitated twice or for three times by the same method, and the finally obtained precipitates are dried to obtain the degradable polyester used in the absorbable iron-based device of the present application.

Gel permeation chromatography (GPC for short) specifically includes the following steps that: the degradable polyester raw material is dissolved into the good solvent (such as ethyl acetate, tetrahydrofuran, acetone, dichloromethane or chloroform) for the degradable polyester to obtain the degradable polyester solution; the degradable polyester solution is injected into a GPC column (such as a PL MIXED-C type GPC preparation column of Agilent Company) through a liquid phase sample injection pump, and the degradable polyester in the degradable polyester solution flows out in sequence according to the molecular weights from large to small after passing through the GPC column; and the effluent is retained for a certain period of time, and then dried to obtain the degradable polyester used in the absorbable iron-based device of the present application.

An ultrafiltration membrane filtration method specifically includes the following steps: the degradable polyester raw material is dissolved into the good solvent (such as ethyl acetate, tetrahydrofuran, acetone, dichloromethane or chloroform) for the degradable polyester to obtain the degradable polyester solution; the degradable polyester solution is pressurized and allowed to pass through an ultrafiltration membrane; at the moment, most of the residual monomer and the low molecular weight portion in the degradable polyester and the solvent may pass through the ultrafiltration membrane, and a high-molecular-weight portion and a little of the residual monomer and the low molecular weight portion are retained on the surface of the ultrafiltration membrane; and the filter residues retained on the surface of the ultrafiltration membrane are dried to obtain the degradable polyester used in the absorbable iron-based device of the present application.

An extraction method specifically includes the following steps: the degradable polyester raw material is immersed in the poor solvent (such as water, methanol, ethanol and isopropanol) for the degradable polyester, and the degradable polyester is removed after certain time and then dried to obtain the degradable polyester used in the absorbable iron-based device of the present application.

To understand the objectives, technical solutions and advantages of the present application more clearly, the technical solution of the present application is further described below in detail through specific embodiments. It should be understood that the specific embodiments described herein are merely explanatory of the present application, but not intended to limit the present application.

Unless otherwise defined, all technical and scientific terms used herein are the same as meanings of general understandings of those skilled in the art of the present application. The terms used in the description of the text are only used to describe the specific embodiments, but not intended to limit the present application.

Embodiment 1

Figure 1:
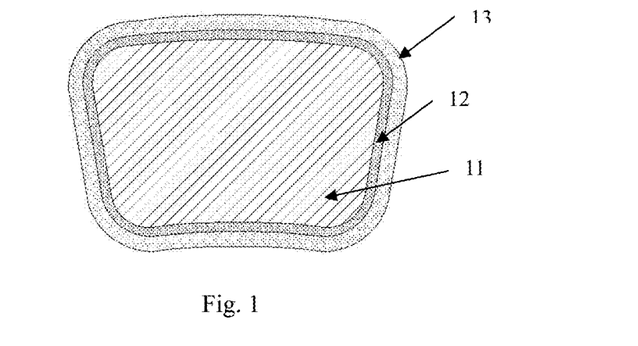
FIG. 1 is a sectional view of a stent strut of an absorbable iron-based stent provided by Embodiment 1 on a section perpendicular to an axial direction of the stent.

An absorbable iron-based stent provided by Embodiment 1 is composed of multiple stent struts. Referring to FIG. 1, each stent strut includes an iron-based substrate 11, a zinc-containing protector 12 completely covering the iron-based substrate 11, and a degradable polyester coating layer 13 completely covering the zinc-containing protector 12. The iron-based substrate 11 is made of an iron-based alloy having a carbon content of 1.19 percent. The zinc-containing protector 12 is a zinc elementary substance plating layer. The degradable polyester coating layer 13 is poly-D,L-lactic acid including a low molecular weight portion having a molecular weight less than 10,000 and a mass fraction of 2 percent and a residual monomer having a mass fraction of 1.6 percent.

A manufacturing process for the absorbable iron-based stent provided by Embodiment 1 was as follows:

the surface of an iron-based stent having an original radial supporting force of 145 kPa and a mass of 4.5 mg was uniformly plated with a zinc elementary substance serving as a zinc-containing protector by a vacuum evaporation method, so as to obtain a zinc-plated iron-based stent in which the zinc elementary substance completely covers the surface of the iron-based stent and the ratio of the mass of the zinc elementary substance to the mass of the iron-based stent is 1:2; poly-D,L-lactic acid was separated and purified through GPC to obtain poly-D,L-lactic acid including a low molecular weight portion having a molecular weight less than 10,000 and a mass fraction of 2 percent and a residual monomer having a mass fraction of 1.6 percent; the obtained poly-D,L-lactic acid was dissolved in ethyl acetate to obtain a coating layer solution; the coating layer solution was sprayed onto the surface of the zinc-plated iron-based stent, the ratio of the mass of the poly-D,L-lactic acid to the mass of the iron-based stent is 1:10, and then the surface was dried to remove the ethyl acetate; and the stent was pressed by a pressing equipment and then sterilized with ethylene oxide, thus the absorbable iron-based stent of Embodiment 1 was obtained.

Figure 2:
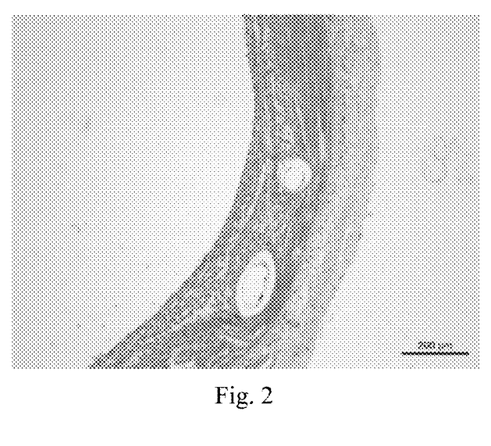
FIG. 2 is an H&E staining graph of a pathological section of a tissue around the stent when the absorbable iron-based stent provided by Embodiment 1 has been implanted into a coronary artery of a pig for 1 month.

A total of nine absorbable iron-based stents identical to the absorbable iron-based stent of Embodiment 1 were manufactured by adopting the same materials and method; three of the absorbable iron-based stents were randomly respectively implanted into the left anterior descending artery, the right main coronary artery and the left circumflex artery of a coronary artery of a small pig, and a passing-expansion ratio was kept between 1.1:1 and 1.2:1 in the implantation process; and after 1 month, the stents and peripheral tissues thereof were removed for H&E staining and pathological analysis, and a pathological section of the peripheral tissue of the stent was as shown in FIG. 2. A pathological analysis result shows that when the absorbable iron-based stents provided by Embodiment 1 have been implanted into the body of an animal for 1 month, zinc ions released in the corroding process of the zinc-containing protectors are at a proper concentration and do not generate cytotoxicity to the peripheral tissues.

The remaining six absorbable iron-based stents were respectively implanted into the abdominal aortas of two New Zealand rabbits having similar ages and weights in such a way that three absorbable iron-based stents were randomly implanted into the body of each rabbit; then the two New Zealand rabbits were sampled respectively when the stents had been implanted for 6 months and 24 months; and the three stents removed during sampling at each time were respectively subjected to radial supporting force test and mass retention rate test of the degradable polyester. Test results are as follows: when the stents have been implanted for 6 months, the mean value of the radial supporting forces of the stents is 140 kPa, and the mean value of the mass retention rates of the degradable polyester is 61 percent. When the stents have been implanted for 24 months, the stents are completely corroded.

The above results show that when the absorbable iron-based stent provided by the present embodiment has been implanted into the body of the animal for 1 month, the zinc ions released in the corroding process of the zinc-containing protector is at the proper concentration and does not generate the cytotoxicity to the peripheral tissue; when the stent has been implanted into the body of the animal for 6 months, the radial supporting force of the stent may meet the clinical requirement for a vascular stent (namely more than or equal to 55 kPa), and the mass retention rate of the residual degradable polyester on the stent is more than 30 percent, which may accelerate the corrosion of the iron-based stent; and when implanted for 24 months, the stent is completely corroded, so as to avoid long-term adverse reactions caused by the long-term retention of the implant in the body of the animal.

Embodiment 2

The surface of an iron-based stent having an original radial supporting force of 145 kPa and a mass of 4.5 mg was uniformly plated with a zinc elementary substance serving as a zinc-containing protector by a vacuum evaporation method, so as to obtain a zinc-plated iron-based stent in which the zinc elementary substance completely covers the surface of the iron-based stent and the ratio of the mass of the zinc elementary substance to the mass of the iron-based stent is 1:200; poly-D,L-lactic acid was separated and purified through GPO to obtain poly-D,L-lactic acid including a low molecular weight portion having a molecular weight less than 10,000 and a mass fraction of 2 percent and a residual monomer having a mass fraction of 1.6 percent; the obtained poly-D,L-lactic acid was dissolved in ethyl acetate to obtain a coating layer solution; the coating layer solution was sprayed onto the surface of the zinc-plated iron-based stent, the ratio of the mass of the poly-D,L-lactic acid to the mass of the iron-based stent is 1:10, and then the surface was dried to remove the ethyl acetate; and the stent was pressed by a pressing equipment and then sterilized with ethylene oxide, thus the absorbable iron-based stent of Embodiment 2 was obtained.

A total of six absorbable iron-based stents identical to the absorbable iron-based stent of Embodiment 2 were manufactured by adopting the same materials and method; the six absorbable iron-based stents were respectively implanted into the abdominal aortas of two New Zealand rabbits having similar ages and weights in such a way that three absorbable iron-based stents were randomly implanted into the body of each rabbit; then the two New Zealand rabbits were sampled respectively when the stents have been implanted for 6 months and 24 months; and the three stents removed during sampling at each time were respectively subjected to radial supporting force test and mass retention rate test of the degradable polyester. Test results are as follows: when the stents have been implanted for 6 months, the mean value of the radial supporting forces of the stents is 80 kPa which meets the clinical requirement for a vascular stent, and the mean value of the mass retention rates of the degradable polyester is 47 percent. When the stents have been implanted for 24 months, the stents are completely corroded.

Embodiment 3

The surface of an iron-based stent having an original radial supporting force of 145 kPa and the mass of 4.5 mg was uniformly plated with a zinc elementary substance serving as a zinc-containing protector by a vacuum evaporation method, so as to obtain a zinc-plated iron-based stent in which the zinc elementary substance completely covers the surface of the iron-based stent and the ratio of the mass of the zinc elementary substance to the mass of the iron-based stent is 1:20; poly-D,L-lactic acid was separated and purified through GPC to obtain poly-D,L-lactic acid including a low molecular weight portion having a molecular weight less than 10,000 and a mass fraction of 2 percent and a residual monomer having a mass fraction of 1.6 percent; the obtained poly-D,L-lactic acid was dissolved in ethyl acetate to obtain a coating layer solution; the coating layer solution was sprayed onto the surface of the zinc-plated iron-based stent, the ratio of the mass of the poly-D,L-lactic acid to the mass of the iron-based stent is 1:10, and then the surface was dried to remove the ethyl acetate; and the stent was pressed by a pressing equipment and then sterilized with ethylene oxide, thus the absorbable iron-based stent of Embodiment 3 was obtained.

Figure 3:
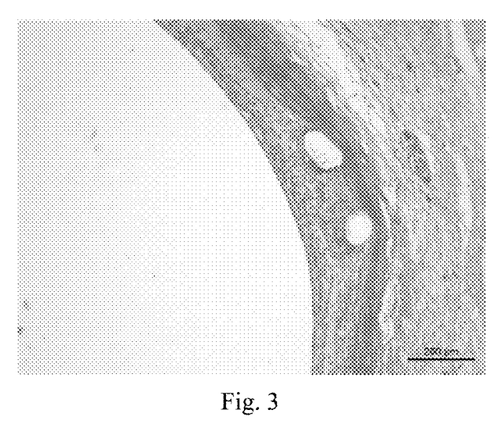
FIG. 3 is an H&E staining graph of a pathological section of a tissue around a stent when an absorbable iron-based stent provided by Embodiment 3 has been implanted into a coronary artery of a pig for 1 month.

A total of nine absorbable iron-based stents identical to the absorbable iron-based stent of Embodiment 3 were manufactured by adopting the same materials and method; three of the absorbable iron-based stents were respectively implanted into the left anterior descending artery, the right main coronary artery and the left circumflex artery of a coronary artery of a small pig, and a passing-expansion ratio was kept between 1.1:1 and 1.2:1 in the implantation process; and after 1 month, the stents and peripheral tissues thereof were removed for H&E staining and pathological analysis, and a pathological section of the peripheral tissue of the stent was as shown in FIG. 3. A pathological analysis result shows that when the absorbable iron-based stent provided by Embodiment 3 has been implanted into the body of an animal for 1 month, no tissue abnormality phenomenon occurs in the peripheral tissue of the stent.

The remaining six absorbable iron-based stents were respectively implanted into the abdominal aortas of two New Zealand rabbits having similar ages and weights in such a way that three absorbable iron-based stents were randomly implanted into the body of each rabbit; then the two New Zealand rabbits were sampled respectively when the stents have been implanted for 6 months and 24 months; and the three stents removed during sampling at each time were respectively subjected to radial supporting force test and mass retention rate test of the degradable polyester. Test results are as follows: when the stents have been implanted for 6 months, the mean value of the radial supporting forces of the stents is 100 kPa which meets the clinical requirement for a vascular stent, and the mean value of the mass retention rates of the degradable polyester is 54 percent. When the stents have implanted for 24 months, the stents are completely corroded.

Embodiment 4

Part of the surface of an iron-based stent having an original radial supporting force of 145 kPa and the mass of 4.5 mg were plated with a zinc elementary substance serving as a zinc-containing protector by an electroplating method, so as to obtain a zinc-plated iron-based stent in which the zinc elementary substance only covers part of the surface of the iron-based stent and the ratio of the mass of the zinc elementary substance to the mass of the iron-based stent is 1:50; commercially available poly(butylene succinate) (the mass fraction of its residual monomer was measured at 0.5 percent by the above-mentioned method) was dissolved in ethyl acetate to obtain a coating layer solution; the coating layer solution was sprayed onto the whole surface of the zinc-plated iron-based stent, the ratio of the mass of the poly(butylene succinate) to the mass of the iron-based stent is 1:20, and then the surface were dried to remove the ethyl acetate; and the stent was pressed by a pressing equipment and then sterilized with ethylene oxide, thus the absorbable iron-based stent of Embodiment 4 was obtained.

A total of six absorbable iron-based stents identical to the absorbable iron-based stent of Embodiment 4 were manufactured by adopting the same materials and method; the six absorbable iron-based stents were respectively implanted into the abdominal aortas of two New Zealand rabbits of similar ages and weights in such a way that three absorbable iron-based stents were randomly implanted into the body of each rabbit; then the two New Zealand rabbits were sampled respectively when the stents have been implanted for 6 months and 24 months; and the three stents removed during sampling at each time were respectively subjected to radial supporting force test and mass retention rate test of the degradable polyester. Test results are as follows: when the stents have been implanted for 6 months, the mean value of the radial supporting forces of the stents is 80 kPa which meets the clinical requirement for a vascular stent, and the mean value of the mass retention rates of the degradable polyester is 30 percent. When the stents have been implanted for 24 months, the stents are completely corroded.

Embodiment 5

The surface of an iron-based stent having an original radial supporting force of 145 kPa and the mass of 4.5 mg was uniformly plated with a zinc alloy having a zinc content of 98.7 percent and serving as a zinc-containing protector by a vacuum evaporation method, so as to obtain a zinc-plated iron-based stent in which the zinc alloy completely covers the surface of the iron-based stent and the ratio of the mass of zinc in the zinc alloy to the mass of the iron-based stent is 1:10; polycaprolactone was separated and purified through a precipitation method to obtain polycaprolactone including a low molecular weight portion having a molecular weight less than 10,000 and a mass fraction of 5 percent and a residual monomer having a mass fraction of 0.1 percent; the obtained polycaprolactone and sirolimus were mixed according to a mass ratio of 0.2:1 and then were dissolved in ethyl acetate to obtain a polyester-drug solution; the surface of the zinc-plated iron-based stent was dropwise coated with the polyester-drug solution, the ratio of the mass of the polycaprolactone to the mass of the iron-based stent is 1:50, and then was dried to remove the ethyl acetate; and the stent was pressed by a pressing equipment and then sterilized with ethylene oxide, thus the absorbable iron-based stent of Embodiment 5 was obtained.

A total of six absorbable iron-based stents identical to the absorbable iron-based stent of Embodiment 5 were manufactured by adopting the same materials and method; the six absorbable iron-based stents were respectively implanted into the abdominal aortas of two New Zealand rabbits of similar ages and weights in such a way that three absorbable iron-based stents were randomly implanted into the body of each rabbit; then the two New Zealand rabbits were sampled respectively when the stents have been implanted for 6 months and 24 months; and the three stents removed during sampling at each time were respectively subjected to radial supporting force test and mass retention rate test of degradable polyester. Test results are as follows: when the stents have been implanted for 6 months, the mean value of the radial supporting forces of the stents is 140 kPa which meets the clinical requirement for a vascular stent, and the mean value of the mass retention rates of the degradable polyester is 65 percent. When the stents have been implanted for 24 months, the stents are completely corroded.

Embodiment 6

A plurality of grooves were engraved in the stent struts of an iron-based stent having an original radial supporting force of 145 kPa and the mass of 4.5 mg through laser and were filled with a zinc elementary substance serving as a zinc-containing protector, so as to obtain a zinc-containing iron-based stent in which the ratio of the mass of the zinc elementary substance to the mass of the iron-based stent is 1:200; a polylactic-glycolic acid copolymer was separated and purified through an extraction method to obtain polylactic-glycolic acid including a low molecular weight portion having a molecular weight less than 100,000 and a mass fraction of 4.1 percent and a residual monomer having a mass fraction of 2 percent; the obtained polylactic-glycolic acid, taxol and dexamethasone were mixed according to a mass ratio of 1:1:1 and then were dissolved in ethyl acetate to obtain a polyester-drug solution; the surface of the zinc-containing iron-based stent was brushed with the polyester-drug solution, the ratio of the mass of the polylactic-glycolic acid to the mass of the iron-based stent is 1:100, and then was dried to remove the ethyl acetate; and the stent was pressed by a pressing equipment and then sterilized with ethylene oxide, thus the absorbable iron-based stent of Embodiment 6 was obtained.

A total of six absorbable iron-based stents identical to the absorbable iron-based stent of Embodiment 6 were manufactured by adopting the same materials and method; the six absorbable iron-based stents were respectively implanted into the abdominal aortas of two New Zealand rabbits of similar ages and weights in such a way that three absorbable iron-based stents were randomly implanted into the body of each rabbit; then the two New Zealand rabbits were sampled respectively when the stents have been implanted for 6 months and 24 months; and the three stents removed during sampling at each time were respectively subjected to radial supporting force test and mass retention rate test of degradable polyester. Test results are as follows: when the stents have been implanted for 6 months, the mean value of the radial supporting forces of the stents is 100 kPa which meets the clinical requirement for a vascular stent, and the mean value of the mass retention rates of the degradable polyester is 70 percent. When the stents have been implanted for 24 months, the stents are completely corroded.

Embodiment 7

The surface of an iron-based stent having an original radial supporting force of 145 kPa and a mass of 4.5 mg was uniformly plated with a zinc elementary substance serving as a zinc-containing protector by an electroplating method, so as to obtain a zinc-plated iron-based stent in which the zinc elementary substance only covers part of the surface of the iron-based stent and the ratio of the mass of zinc elementary substance to the mass of the iron-based stent is 1:20; polylactic acid was separated and purified through an ultrafiltration membrane filtration method to obtain polylactic acid including a low molecular weight portion having a molecular weight less than 100,000 and a mass fraction of 2 percent and a residual monomer having a mass fraction of 0.5 percent; the obtained polylactic acid and sirolimus were mixed according to a mass ratio of 10:1 and then were dissolved in ethyl acetate to obtain a polyester-drug solution; the polyester-drug solution is sprayed onto the surface of the zinc-plated iron-based stent, the ratio of the mass of the polylactic acid to the mass of the iron-based stent is 1:10, and then the surface was dried to remove the ethyl acetate; and the stent was pressed by a pressing equipment and then sterilized with ethylene oxide, thus the absorbable iron-based stent of Embodiment 7 was obtained.

A totally six absorbable iron-based stents identical to the absorbable iron-based stent of Embodiment 7 were manufactured by adopting the same materials and method; the six absorbable iron-based stents were respectively implanted into the abdominal aortas of two New Zealand rabbits of similar ages and weights in such a way that three absorbable iron-based stents were randomly implanted into the body of each rabbit; then the two New Zealand rabbits were sampled respectively when the stents were implanted for 6 months and 24 months; and the three stents removed during sampling at each time were respectively subjected to radial supporting force test and mass retention rate test of degradable polyester. Test results are as follows: when the stents have been implanted for 6 months, the mean value of the radial supporting forces of the stents is 100 kPa which meets the clinical requirement for a vascular stent, and the mean value of the mass retention rates of the degradable polyester is 52 percent. When the stents have been implanted for 24 months, the stents are completely corroded.

Embodiment 8

A plurality of blind holes were engraved in the stent struts of an iron-based stent having an original radial supporting force of 145 kPa and the mass of 4.5 mg through laser, and part of the blind holes were filled with a zinc elementary substance serving as a zinc-containing protector, so as to obtain a zinc-containing iron-based stent where the ratio of the total mass of the filled zinc elementary substance to the mass of the iron-based stent is 1:100; polylactic acid was separated and purified through GPO to obtain polylactic acid including a low molecular weight portion having a molecular weight less than 100,000 and a mass fraction of 1 percent and a residual monomer having a mass fraction of 2.5 percent; the obtained polylactic acid, chitosan, heparin and cilostazol were mixed according to a mass ratio of 10:0.5:0.5:1, and then the rest of blind holes were filled with the mixture, the ratio of the mass of the polylactic acid to the mass of the iron-based stent is 1:6; and the stent was pressed by a pressing equipment and then sterilized with ethylene oxide, thus the absorbable iron-based stent of Embodiment 8 was obtained.

A total of six absorbable iron-based stents identical to the absorbable iron-based stent of Embodiment 8 were manufactured by adopting the same materials and method; the six absorbable iron-based stents were respectively implanted into the abdominal aortas of two New Zealand rabbits of similar ages and weights in such a way that three absorbable iron-based stents were randomly implanted into the body of each rabbit; then the two New Zealand rabbits were sampled respectively when the stents were implanted for 6 months and 24 months; and the three stents removed during sampling at each time were respectively subjected to radial supporting force test and mass retention rate test of degradable polyester. Test results are as follows: when the stents have been implanted for 6 months, the mean value of the radial supporting forces of the stents is 110 kPa which meets the clinical requirement for a vascular stent, and the mean value of the mass retention rates of the degradable polyester is 38 percent. When the stents have been implanted for 24 months, the stents are completely corroded.

Embodiment 9

The surface of an iron-based stent having an original radial supporting force of 145 kPa and the mass of 4.5 mg was uniformly plated with a zinc alloy having a zinc content of 99.7 percent and serving as a zinc-containing protector by a vacuum evaporation method, so as to obtain a zinc-plated iron-based stent in which the zinc alloy completely covers the surface of the iron-based stent and the ratio of the mass of zinc in the zinc alloy to the mass of the iron-based stent is 1:50; polyglycolic acid was separated and purified through GPO to obtain polyglycolic acid including a low molecular weight portion having a molecular weight less than 10,000 and a mass fraction of 0.5 percent and a residual monomer having a mass fraction of 2.9 percent; the obtained polyglycolic acid and loratadine were mixed according to a mass ratio of 20:1 and then were dissolved in ethyl acetate to obtain a polyester-drug solution; the surface of an inner cavity of the zinc-plated iron-based stent was brushed with the polyester-drug solution, the ratio of the mass of the polyglycolic acid to the mass of the iron-based stent is 1:200, and then was dried to remove the ethyl acetate; and the stent was pressed by a pressing equipment and then sterilized with ethylene oxide, thus the absorbable iron-based stent of Embodiment 9 was obtained.

A total of six absorbable iron-based stents identical to the absorbable iron-based stent of Embodiment 9 were manufactured by adopting the same materials and method; the six absorbable iron-based stents were respectively implanted into the abdominal aortas of two New Zealand rabbits of close ages and weights in such a way that three absorbable iron-based stents were randomly implanted into the body of each rabbit; then the two New Zealand rabbits were sampled respectively when the stents have been implanted for 6 months and 24 months; and the three stents removed during sampling at each time were respectively subjected to radial supporting force test and mass retention rate test of degradable polyester. Test results are as follows: when the stents have been implanted for 6 months, the mean value of the radial supporting forces of the stents is 100 kPa which meets the clinical requirement for a vascular stent, and the mean value of the mass retention rates of the degradable polyester is 65 percent. When the stents have been implanted for 24 months, the stents are completely corroded.

The results show that even if the degradable polyester of the absorbable iron-based stent provided by Embodiment 9 has a relatively high content of the residual monomer, the degradable polyester may still control the corrosion of the zinc-containing protector due to its relatively low content of the low molecular weight portion having a molecular weight less than 10,000, so that the radial supporting force of the stent may still meet the clinical requirement when the stent has been implanted for 6 months; and furthermore, the residual degradable polyester on the stent may accelerate the complete corrosion of the iron-based substrate within 24 months of the implantation.

Embodiment 10

The surface of an iron-based stent having an original radial supporting force of 145 kPa and the mass of 4.5 mg was uniformly plated with a zinc elementary substance serving as a zinc-containing protector by a vacuum evaporation method, so as to obtain a zinc-plated iron-based stent in which the zinc elementary substance completely covers the surface of the iron-based stent and the ratio of the mass of zinc elementary substance to the mass of the iron-based stent is 1:2; polycaprolactone was separated and purified through a precipitation method to obtain polycaprolactone including a low molecular weight portion having a molecular weight less than 100,000 and a mass fraction of 17 percent and a residual monomer having a mass fraction of 0.8 percent; the obtained polycaprolactone, carbonic ester and hydrocortisone were mixed according to a mass ratio of 20:1:1 and then were dissolved in ethyl acetate to obtain a polyester-drug solution; polyester-drug solution is sprayed onto the surface of the zinc-plated iron-based stent, the ratio of the mass of the polycaprolactone to the mass of the iron-based stent is 1:1, and then the surface was dried to remove the ethyl acetate; and the stent was pressed by a pressing equipment and then sterilized with ethylene oxide, thus the absorbable iron-based stent of Embodiment 10 was obtained.

A total of six absorbable iron-based stents identical to the absorbable iron-based stent of Embodiment 10 were manufactured by adopting the same materials and method; the six absorbable iron-based stents were respectively implanted into the abdominal aortas of two New Zealand rabbits of similar ages and weights in such a way that three absorbable iron-based stents were randomly implanted into the body of each rabbit; then the two New Zealand rabbits were sampled respectively when the stents have been implanted for 6 months and 24 months; and the three stents removed during sampling at each time were respectively subjected to radial supporting force test and mass retention rate test of degradable polyester. Test results are as follows: when the stents have been implanted for 6 months, the mean value of the radial supporting forces of the stents is 110 kPa which meets the clinical requirement for a vascular stent, and the mean value of the mass retention rates of the degradable polyester is 46 percent. When the stents have been implanted for 24 months, the stents are completely corroded.

The results show that even if the degradable polyester of the absorbable iron-based stent provided by Embodiment 10 has a relatively high content of the low molecular weight portion, the degradable polyester may still control the corrosion of the zinc-containing protector due to its relatively low content of the residual monomer after the stent has been implanted, so that the radial supporting force of the stent may still meet the clinical requirement when the stent has been implanted for 6 months, and furthermore, the residual degradable polyester on the stent may accelerate complete corrosion of the iron-based substrate within 24 months of the implantation.

Contrast 1

The surface of an iron-based stent having an original radial supporting force of 145 kPa and the mass of 4.5 mg was uniformly plated with a zinc elementary substance serving as a zinc-containing protector by a vacuum evaporation method, so as to obtain a zinc-plated iron-based stent in which the zinc elementary substance completely covers the surface of the iron-based stent and the ratio of the mass of the zinc elementary substance to the mass of the iron-based stent is 1:1.5; poly-D,L-lactic acid was separated and purified through GPC to obtain poly-D,L-lactic acid including a low molecular weight portion having a molecular weight less than 10,000 and a mass fraction of 2 percent and a residual monomer having a mass fraction of 1.6 percent; the obtained poly-D,L-lactic acid was dissolved in ethyl acetate to obtain a coating layer solution; the coating layer solution was sprayed onto the surface of the zinc-plated iron-based stent, the ratio of the mass of the poly-D,L-lactic acid to the mass of the iron-based stent is 1:10, and then the surface was dried to remove the ethyl acetate; and the stent was pressed by a pressing equipment and then sterilized with ethylene oxide, thus the absorbable iron-based stent of Contrast 1 was obtained.

Figure 4:
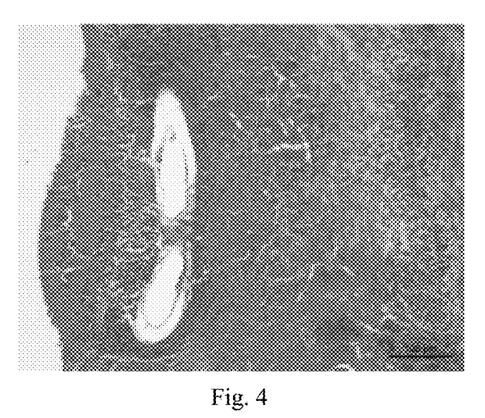
FIG. 4 is an H&E staining graph of a pathological section of a tissue around a stent when an absorbable iron-based stent of Contrast 1 has been implanted into a coronary artery of a pig for 1 month.

A total of three absorbable iron-based stents identical to the absorbable iron-based stent of Contrast 1 were manufactured by adopting the same materials and method; the three absorbable iron-based stents were respectively implanted into the left anterior descending artery, the right main coronary artery and the left circumflex artery of a coronary artery of a small pig, and a passing-expansion ratio was kept between 1.1:1 and 1.2:1 in the implantation process; and after 1 month, the stents and peripheral tissues thereof were removed for H&E staining and pathological analysis, and a pathological section of the peripheral tissue of the stent was as shown in FIG. 4. A pathological analysis result shows that when the absorbable iron-based stent of Contrast 1 has been implanted into the body of an animal for 1 month, the peripheral tissue of the stent is severely damaged to cause infiltration of a large number of inflammatory cells.

The result shows that when compared with the absorbable iron-based stent provided by Embodiment 1, the absorbable iron-based stent of Contrast 1 suffers from the defect that the ratio of the mass of the zinc-containing protector to the mass of the iron-based stent is relatively large, so the corrosion of the zinc-containing protector produces a large number of zinc ions that generate the cytotoxicity to the peripheral tissue after the stent of Contrast 1 has been implanted into the body of the animal.

Contrast 2

The surface of an iron-based stent having an original radial supporting force of 145 kPa and the mass of 4.5 mg was uniformly plated with a zinc elementary substance serving as a zinc-containing protector by a vacuum evaporation method, so as to obtain a zinc-plated iron-based stent in which the zinc elementary substance completely covers the surface of the iron-based stent and the ratio of the mass of the zinc elementary substance to the mass of the iron-based stent is 1:250; poly-D,L-lactic acid was separated and purified through GPC to obtain poly-D,L-lactic acid including a low molecular weight portion having a molecular weight less than 10,000 and a mass fraction of 2 percent and a residual monomer having a mass fraction of 1.6 percent; the obtained poly-D,L-lactic acid was dissolved in ethyl acetate to obtain a coating layer solution; the coating layer solution was sprayed onto the surface of the zinc-plated iron-based stent, the ratio of the mass of the poly-D,L-lactic acid to the mass of the iron-based stent is 1:10, and then the surface was dried to remove the ethyl acetate; and the stent was pressed by a pressing equipment and then sterilized with ethylene oxide, thus the absorbable iron-based stent of Contrast 2 was obtained.

Figure 5:
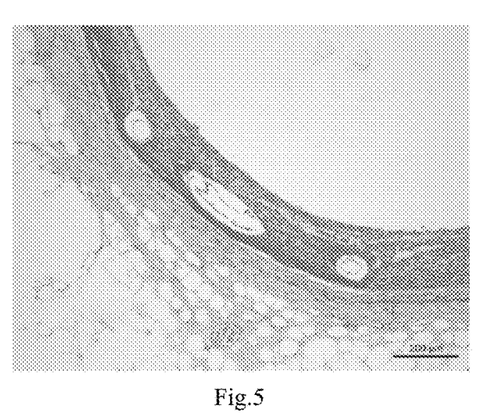
FIG. 5 is an H&E staining graph of a pathological section of a tissue around a stent when an absorbable iron-based stent of Contrast 2 has been implanted into a coronary artery of a pig for 1 month.

A total of six absorbable iron-based stents identical to the absorbable iron-based stent of Contrast 2 were manufactured by adopting the same materials and method. Three of the absorbable iron-based stents were randomly respectively implanted into the left anterior descending artery, the right main coronary artery and the left circumflex artery of a coronary artery of a small pig, and a passing-expansion ratio was kept between 1.1:1 and 1.2:1 in the implantation process; and after 1 month, the stents and peripheral tissues thereof were removed for H&E staining and pathological analysis, and a pathological section of the peripheral tissue of the stent was as shown in FIG. 5. A pathological analysis result shows that when the absorbable iron-based stent of Contrast 2 has been implanted into the body of an animal for 1 month, no tissue abnormality phenomenon occurs in the peripheral tissue of the stent.

The remaining three absorbable iron-based stents were implanted into the abdominal aorta of one New Zealand rabbit; then the New Zealand rabbit was sampled when the stents were implanted for 6 months; and the three stents removed during sampling were respectively subjected to radial supporting force test and mass retention rate test of degradable polyester. Test results are as follows: when the stents have been implanted for 6 months, the stent struts are broken, and the mean value of the radial supporting forces of the stents is 48 kPa which does not meet the clinical requirement for a vascular stent, and the mean value of the mass retention rates of the degradable polyester is 45 percent.

The result shows that when compared with the absorbable iron-based stent provided by Embodiment 2, the absorbable iron-based stent of Contrast 2 suffers from the defects that the zinc-containing protector has been completely corroded within 1 month of implantation due to its relatively small mass, the complete corrosion of the zinc-containing protector leads to corrosion of the iron-based substrate; and when the stent has been implanted for 6 months, the iron-based substrate is severely corroded so that the stent struts break, and the stent does not maintain an effective radial support.

Contrast 3

The surface of an iron-based stent having an original radial supporting force of 145 kPa and the mass of 4.5 mg was uniformly plated with a zinc elementary substance serving as a zinc-containing protector by a vacuum evaporation method, so as to obtain a zinc-plated iron-based stent in which the zinc elementary substance completely covers the surface of the iron-based stent and the ratio of the mass of the zinc elementary substance to the mass of the iron-based stent is 1:20; commercially available poly-D,L-lactic acid (the mass fraction of the low molecular weight portion having a molecular weight less than 10,000 was measured at 17 percent and the mass fraction of the residual monomer was measured at 2.9 percent through the above-mentioned method) was dissolved in ethyl acetate to obtain a coating layer solution; the coating layer solution was sprayed onto the surface of the zinc-plated iron-based stent, the ratio of the mass of the polylactic acid to the mass of the iron-based stent is 1:10, and then the surface was dried to remove the ethyl acetate; and the stent was pressed by a pressing equipment and then sterilized with ethylene oxide, thus the absorbable iron-based stent of Contrast 3 was obtained.

Figure 6:
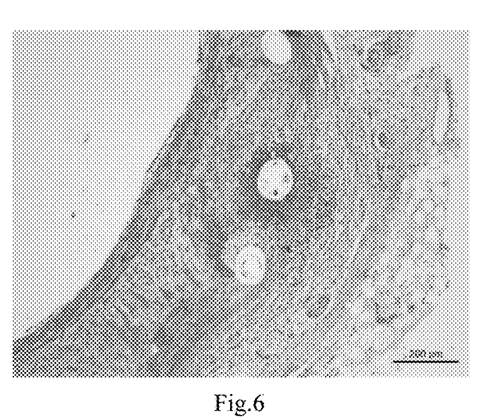
FIG. 6 is an H&E staining graph of a pathological section of a tissue around a stent when an absorbable iron-based stent of Contrast 3 has been implanted into a coronary artery of a pig for 1 month.

A total of nine absorbable iron-based stents identical to the absorbable iron-based stent of Contrast 3 were manufactured by adopting the same materials and method; three of the absorbable iron-based stents were randomly respectively implanted into the left anterior descending artery, the right main coronary artery and the left circumflex artery of a coronary artery of a small pig, and a passing-expansion ratio was kept between 1.1:1 and 1.2:1 in the implantation process; and after 1 month, the stents and peripheral tissues thereof were removed for H&E staining and pathological analysis, and a pathological section of the peripheral tissue of the stent was as shown in FIG. 6. A pathological analysis result shows that when the absorbable iron-based stent of Contrast 3 has been implanted into the body of an animal for 1 month, there are inflammatory cells surrounding part of the stent, indicating that the tissue is slightly damaged.

The remaining six absorbable iron-based stents were respectively implanted into the abdominal aortas of two New Zealand rabbits having the same ages and weights in such a way that three absorbable iron-based stents were randomly implanted into the body of each rabbit; then the two New Zealand rabbits were sampled respectively when the stents were implanted for 6 months and 24 months; and the three stents removed during sampling at each time were respectively subjected to radial supporting force test and mass retention rate test of degradable polyester. Test results are as follows: when the stents have been implanted for 6 months, the stent struts are not broken, and the mean value of the radial supporting forces of the stents is 60 kPa which basically meets the clinical requirement for a vascular stent, but the mean value of the mass retention rates of the degradable polyester is only 20 percent. When the stents have been implanted for 24 months, the stents are not completely corroded, and it is measured that the mass loss rate of the iron-based substrate is 60 percent.

The result shows that when compared with the absorbable iron-based stent provided by Embodiment 3, the absorbable iron-based stent of Contrast 3 suffers from the defects that the relatively high mass fraction of the low molecular weight portion and the relatively high content of the residual monomer in the degradable polyester lead to a relatively high acidity around the stent within 1 month of the implantation, so that the zinc-containing protector covering the surface of the iron-based substrate is corroded at a relatively high speed during the early stages of implantation to produce a large number of zinc ions that generate slight cytotoxicity to the peripheral tissue; and in addition, the relatively high acidity environment also leads to fast degradation of the degradable polyester during the early stages of implantation, so that the mass retention rate of the degradable polyester at the sixth month of the implantation is relatively low, and the corrosion of the iron-based substrate after 6 months of the implantation may not be accelerated, resulting in a portion of the iron-based substrate remaining in the body of the animal after the stent has been implanted for 24 months.

Contrast 4

The surface of an iron-based stent having an original radial supporting force of 145 kPa and the mass of 4.5 mg was uniformly plated with a zinc elementary substance serving as a zinc-containing protector by a vacuum evaporation method, so as to obtain a zinc-plated iron-based stent in which the zinc elementary substance completely covers the surface of the iron-based stent and the ratio of the mass of the zinc elementary substance to the mass of the iron-based stent is 1:200; commercially available poly-D,L-lactic acid (the mass fraction of the low molecular weight portion having the molecular weight less than 10,000 was 17 percent and the mass fraction of the residual monomer was t 2.9 percent measured by the above-mentioned method) was dissolved in ethyl acetate to obtain a coating layer solution; the coating layer solution was sprayed onto the surface of the zinc-plated iron-based stent, the ratio the mass of the poly-D, L-lactic acid to the mass of the iron-based stent is 1:10, and then the surface was dried to remove the ethyl acetate; and the stent was pressed by a pressing equipment and then sterilized with ethylene oxide, thus the absorbable iron-based stent of Contrast 4 was obtained.

Figure 7:
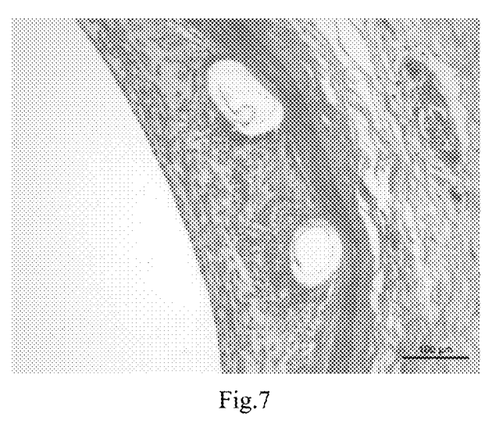
FIG. 7 is an H&E staining graph of a pathological section of a tissue around a stent when an absorbable iron-based stent of Contrast 4 has been implanted into a coronary artery of a pig for 1 month.

A totally six absorbable iron-based stents identical to the absorbable iron-based stent of Contrast 4 were manufactured by adopting the same materials and method. Three of the absorbable iron-based stents were respectively implanted into the left anterior descending artery, the right main coronary artery and the left circumflex artery of a coronary artery of a small pig, and a passing-expansion ratio was kept between 1.1:1 and 1.2:1 in the implantation process; and after 1 month, the stents and peripheral tissues thereof were removed for H&E staining and pathological analysis, and a pathological section of the peripheral tissue of the stent was as shown in FIG. 7. A pathological analysis result shows that when the absorbable iron-based stent of Contrast 4 has been implanted into the body of an animal for 1 month, no tissue abnormality phenomenon occurs in the peripheral tissue of the stent.

The remaining three absorbable iron-based stents were implanted into the abdominal aorta of a New Zealand rabbit; then the New Zealand rabbit was sampled when the stents were implanted for 6 months; and the three stents removed after the stents have been implanted for 6 months were respectively subjected to radial supporting force test and mass retention rate test of degradable polyester. Test results are as follows: when the stents have been implanted for 6 months, most of the stent struts are broken, and the mean value of the radial supporting forces of the stents is 30 kPa which does not meet the clinical requirement, and the mean value of the mass retention rates of the degradable polyester is only 20 percent.

The result shows that when compared with the absorbable iron-based stent provided by Embodiment 2, the absorbable iron-based stent of Contrast 4 has a higher mass fraction of the low molecular weight portion and a higher residual monomer content in the degradable polyester. The zinc-containing protector is completely corroded during the early stages of implantation, and the iron-based substrate which is protected by the zinc-containing protector is also severely corroded within 6 months after implantation, and the stent struts are broken and may not maintain an effective radial support.

In conclusion, in the absorbable implanted device provided by the present application, the degradation process of the degradable polyester is controlled by adjusting the content of the residual monomer in the degradable polyester or the content of the low molecular weight portion in the degradable polyester, and then the corroding processes of the zinc-containing protector and the iron-based substrate during the early stages of implantation are controlled. Specifically, within 1 to 6 months of the implantation of the device, the degradable polyester promotes the zinc-containing protector to be corroded at a proper rate to allow the zinc-containing protector to be completely corroded within 1 to 6 months after the implantation, and allow the iron-based substrate to be slowly corroded, and even not corroded, under the protection of the zinc-containing protector, so as to meet the clinical requirements for the mechanical property of the implantable device during the early stages of implantation. Meanwhile, during the corroding process of the zinc-containing protector, production of a large number of zinc ions may be avoided, so as to avoid the influence on the safety and effectiveness of the device caused by the cytotoxicity generated by a large number of zinc ions. Furthermore, after the device has been implanted for 1 to 6 months, the mass retention rate of the degradable polyester is more than or equal to 30 percent, so as to ensure that there is still sufficient degradable polyester to accelerate the corrosion of the iron-based substrate during the later stages of the implantation, so as to reduce the possibility of the adverse reactions caused by the long-term retention of the iron-based substrate in the human body.

It should be noted that in Embodiments 1 to 10, the specific implementation modes of the present application are schematically described only through a vascular stent. The technical solutions provided by the present application may also be applied to other implantable devices, such as other luminal stents (such as: a tracheal stent, an esophageal stent, a urethral stent, an intestinal stent or a biliary stent), other cardiovascular implants (such as: a heart occluder, a blood vessel filter and a vascular plug), an orthopaedic implant (such as: a fixing screw, a fixing rivet or a bone plate), a gynecological implant, an andrological implant, a respiratory implant, a dental implant, a suture or a bolt.

The embodiments of the present application are described above, but the present application is not limited to the above-mentioned specific implementation modes. The above-mentioned specific implementation modes are only schematic, but not restrictive. Those of ordinary skill in the art can further make many forms under the enlightenment of the present application without departing from the objective of the present application and the scope protected by claims, and these forms shall all fall within the protection of the present application.

The invention claimed is:

1. An absorbable iron-based device, comprising an iron-based substrate, a zinc-containing protector that completely covers the iron-based substrate, and a degradable polyester in contact with the iron-based substrate and/or the zinc-containing protector, wherein the ratio of the mass of the zinc-containing protector to the mass of the iron-based substrate ranges between 1:200 and 1:2; and wherein the degradable polyester is poly-D,L-lactic acid having a molecular weight less than 10,000, a mass fraction of 2 percent and a residual monomer having a mass fraction of 1.6 percent.

2. The absorbable iron-based device according to claim 1, wherein the degradable polyester is obtained by separating and/or purifying raw materials of the degradable polyester by a precipitation method, gel permeation chromatography, an ultrafiltration film filtration method or an extraction method.

3. The absorbable iron-based device according to claim 1, wherein the ratio of the mass of the degradable polyester to the mass of the iron-based substrate ranges between 1:1 and 1:200.

4. The absorbable iron-based device according to claim 1, wherein the ratio of the mass of the degradable polyester to the mass of the iron-based substrate ranges between 1:6 and 1:100.

5. The absorbable iron-based device according to claim 1, wherein the zinc-containing protector is zinc elementary substance or zinc alloy.

6. The absorbable iron-based device according to claim 1, wherein the degradable polyester is in contact with the iron-based substrate in at least one of the following manners: the degradable polyester at least partially covers the surface of the iron-based substrate; or the iron-based substrate is provided with gaps, grooves or holes, and the degradable polyester is arranged in the gaps, grooves or holes, or the iron-based substrate has an inner cavity, and the inner cavity is filled with the degradable polyester.

7. The absorbable iron-based alloy implanted medical device according to claim 1, wherein the iron-based substrate is made of pure iron or iron-based alloy, and the carbon content of the iron-based alloy is less than or equal to 2.11 percent.

8. The absorbable iron-based device according to claim 1, wherein the absorbable iron-based device further comprises an active drug, and the active drug is mixed with the degradable polyester at a mass ratio of 1:(0.2-20).

9. The absorbable iron-based device according to claim 8, wherein the active drug is selected from the group consisting of a drug for inhibiting vascular proliferation, an antiplatelet drug, an antithrombotic drug, an anti-inflammatory reaction drug or an antisensitization drug; the drug for inhibiting the vascular proliferation is selected from the group consisting of taxol, a taxol derivative, sirolimus or a sirolimus derivative; the antiplatelet drug is cilostazol; the antithrombotic drug is heparin; the anti-inflammatory reaction drug is dexamethasone; and the antisensitization drug is selected from the group consisting of diphenhydramine, chlorpheniramine, promethazine, hydrocortisone, triamcinolone, methylprednisolone, clarityne, fexofenadine, levocetirizine, mizolastine or ebastine.

10. The absorbable iron-based device according to claim 1, wherein the absorbable iron-based device comprises a vascular stent, a non-endovascular stent, an occluder, an orthopaedic implant, a dental implant, a respiratory implant, a gynecological implant, an andrological implant, a suture or a bolt; the non-endovascular stent comprises a tracheal stent, an esophageal stent, a urethral stent, an intestinal stent or a biliary stent; and the orthopaedic implant comprises a fixing screw, a fixing rivet or a bone plate.

* * * * *

UNITED STATES PATENT AND TRADEMARK OFFICE
CERTIFICATE OF CORRECTION

| | | |
|---|---|---|
| PATENT NO. | : 11,684,692 B2 | Page 1 of 1 |
| APPLICATION NO. | : 16/473896 | |
| DATED | : June 27, 2023 | |
| INVENTOR(S) | : Sun et al. | |

It is certified that error appears in the above-identified patent and that said Letters Patent is hereby corrected as shown below:

On the Title Page

Item (73) Assignee, Please change "Lifetech Scientific (Shenzhen) Co., Ltd." to --Biotyx Medical (Shenzhen) Co., Ltd.--.

Signed and Sealed this
Sixteenth Day of September, 2025

Coke Morgan Stewart
*Acting Director of the United States Patent and Trademark Office*